(12) United States Patent
Ichihashi

(10) Patent No.: US 11,009,694 B2
(45) Date of Patent: May 18, 2021

(54) SIDE-VIEWING OPTICAL ADAPTER

(71) Applicant: OLYMPUS CORPORATION, Tokyo (JP)

(72) Inventor: Masaki Ichihashi, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 753 days.

(21) Appl. No.: 15/684,021

(22) Filed: Aug. 23, 2017

(65) Prior Publication Data

US 2017/0371144 A1    Dec. 28, 2017

Related U.S. Application Data

(63) Continuation of application No. PCT/JP2016/083780, filed on Nov. 15, 2016.

(30) Foreign Application Priority Data

Nov. 16, 2015 (JP) .............................. JP2015/224307

(51) Int. Cl.
*A61B 1/00* (2006.01)
*G02B 23/24* (2006.01)
(Continued)

(52) U.S. Cl.
CPC ...... *G02B 23/2476* (2013.01); *A61B 1/00096* (2013.01); *A61B 1/00101* (2013.01);
(Continued)

(58) Field of Classification Search
CPC ................ G02B 23/24; G02B 23/2407; G02B 23/2415; G02B 23/2423; G02B 23/243;
(Continued)

(56) References Cited

U.S. PATENT DOCUMENTS 5,377,669 A * 1/1995 Schulz ............... A61B 1/00142
385/117
5,689,365 A * 11/1997 Takahashi .......... A61B 1/00179
359/362

(Continued)

FOREIGN PATENT DOCUMENTS

JP    2001-147382 A    5/2001
JP    2011-130918 A    7/2011
(Continued)

OTHER PUBLICATIONS

International Search Report dated Jan. 17, 2017 received in PCT/JP2016/083780.

(Continued)

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

An adapter for use with an endoscope. The adapter including: at least first and second axis-shifted lenses, each of the first and second axis-shifted lenses including a truncated portion, the first and second axis shifted lenses being arranged side by side so that respective first and second optical axes are parallel to each other; and a prism arranged further distally than the first and second axis-shifted lenses, the prism being configured to change a viewing direction of each of the first and second axis-shifted lenses; wherein at least a portion of each of the truncated portions of the first and second axis-shifted lenses is arranged further outward in the radial direction than the prism.

9 Claims, 9 Drawing Sheets

(51) Int. Cl.
*G02B 23/26* (2006.01)
*H04N 5/225* (2006.01)

(52) U.S. Cl.
CPC ...... *A61B 1/00177* (2013.01); *A61B 1/00193* (2013.01); *G02B 23/2423* (2013.01); *G02B 23/2484* (2013.01); *G02B 23/2461* (2013.01); *G02B 23/26* (2013.01); *H04N 5/2256* (2013.01); *H04N 2005/2255* (2013.01)

(58) Field of Classification Search
CPC ............ G02B 23/2438; G02B 23/2446; G02B 23/2476; G02B 23/2484; G02B 23/2492; A61B 1/0008; A61B 1/00089; A61B 1/00096; A61B 1/00101; A61B 1/00131; A61B 1/00135; A61B 1/00014; A61B 1/00163; A61B 1/00174; A61B 1/00177; A61B 1/00179; A61B 1/00181; A61B 1/00193; A61B 1/04; A61B 1/042; A61B 1/05; A61B 1/051; A61B 1/053; A61B 1/055; A61B 1/00105; A61B 1/0011; A61B 1/00112; A61B 1/00117; A61B 1/00121; A61B 1/00126; H04N 2005/2255; H04N 5/2257
USPC ........ 600/109–112, 127, 129, 160, 170–175, 600/164–166, 176
See application file for complete search history.

(56) References Cited

U.S. PATENT DOCUMENTS

| | | | |
|---|---|---|---|
| 6,361,491 B1 * | 3/2002 | Hasegawa | A61B 1/00096 348/45 |
| 6,537,209 B1 * | 3/2003 | Pinkhasik | A61B 1/00096 356/241.5 |
| 2002/0161284 A1 * | 10/2002 | Tanaka | A61B 1/00101 600/176 |
| 2003/0125608 A1 | 7/2003 | Igarashi | |
| 2010/0188493 A1 * | 7/2010 | Kanzaki | A61B 1/00059 348/75 |
| 2011/0316029 A1 | 12/2011 | Maruyama et al. | |
| 2012/0029290 A1 | 2/2012 | Nishijima | |
| 2014/0135577 A1 * | 5/2014 | Baumann | G02B 23/243 600/109 |

FOREIGN PATENT DOCUMENTS

| | | |
|---|---|---|
| JP | 2014-124214 A | 7/2014 |
| WO | 2011/108087 A1 | 9/2011 |

OTHER PUBLICATIONS

Notice of Allowance dated Apr. 28, 2020 in Japanese Patent Application No. 2017-551878.

* cited by examiner

SIDE-VIEWING OPTICAL ADAPTER

CROSS-REFERENCE TO RELATED APPLICATIONS

The present application is a continuation of PCT/JP2016/083780, filed on Nov. 15, 2016, which is based upon and claims the benefit of JP 2015-224307, filed on Nov. 16, 2015, the entire contents of each of which is incorporated herein by reference.

BACKGROUND

Field

The present application relates to a side-viewing optical adapter that is attached to an endoscope inserting unit in use.

Background

Conventionally, at the time of inspecting an internal portion of an object to be inspected in medical or industrial application, an endoscope in which a tip end of an elongated endoscope inserting unit is provided with an observation optical system is used. At this time, to obtain an appropriate field of view in accordance with the object to be inspected, an optical adapter is attached to the tip end of the endoscope inserting unit in some cases. The optical adapter is detachably provided at the tip end of the endoscope inserting unit. For example, several types of optical adapters are prepared to change the viewing direction, the observation depth, the field angle, and the like of the observation optical system. When the endoscope is in use, an optical adapter selected as required is attached to the tip end of the inserting unit of the endoscope.

An example of the optical adapter is a side-viewing stereo optical adapter. The stereo optical adapter includes two axis-shifted lenses whose axes are shifted to the right and left from the optical axis. Observation images of the right and left axis-shifted lenses are formed on an image pickup device, which enables the shape and the size of the object to be measured by the principle of triangulation. The side-viewing stereo optical adapter is provided with a prism to bend the viewing direction of the observation optical system 90 degrees to the lateral side of the endoscope inserting unit. In the conventional side-viewing stereo optical adapter, a tip end side of a lens holding frame holding the axis-shifted lenses is provided with a prism holding unit. The prism is arranged in the prism holding unit and held on the tip end surface of the lens holding frame by means of adhesive or the like.

SUMMARY

Accordingly, an adapter for use with an endoscope is provided. The adapter comprising: at least first and second axis-shifted lenses, each of the first and second axis-shifted lenses including a truncated portion, the first and second axis shifted lenses being arranged side by side so that respective first and second optical axes are parallel to each other; a prism arranged further distally than the first and second axis-shifted lenses, the prism being configured to change a viewing direction of each of the first and second axis-shifted lenses; and a holder having a portion configured to attach to and detach from a distal end of the endoscope, the holder including a housing hole in which the first and second axis-shifted lenses are disposed, wherein the housing hole includes first and second cut-out receiving surfaces configured to abut the truncated portion of each of the first and second axis-shifted lenses, respectively, the holder further includes one or more prism positioning surfaces having at least a portion that is further outward in a radial direction than the first and second truncated receiving surfaces, the prism abutting on the one or more prism positioning surfaces to position the prism in the holder, and at least a portion of each of the truncated portions of the first and second axis-shifted lenses is arranged further outward in the radial direction than the prism.

The adapter can further comprises: at least one backside lens arranged proximally to the first and second axis-shifted lenses; and a main body configured to hold the at least one backside lens; wherein the holder having a wall defining the housing hole, the wall having a first portion and a second portion proximal to the first portion; the first portion having a first thickness in a radial direction that is constant in a longitudinal direction of the holder; the second portion having a second thickness in the radial direction greater than the first thickness to form a step at a transition between the first portion and the second portion, the first and second axis-shifted lenses being accommodated in the first portion; and the main body being accommodated in the second portion.

The truncated portion of each of the first and second axis-shifted lenses can form a surface extending in parallel with the optical axis.

The truncated portion of each of the first and second axis-shifted lenses can form a concave surface extending in parallel with the optical axis.

The concave surface can be a curved concave surface.

The first and second of axis-shifted lenses can be arranged so that a distance between center axes of the first and second axis-shifted lenses is equal to or longer than a diameter of each of the first and second axis-shifted lenses.

Also provided is an adapter for use with an endoscope. The adapter comprising: at least first and second axis-shifted lenses, each of the first and second axis-shifted lenses including a truncated portion, the first and second axis shifted lenses being arranged side by side so that respective first and second optical axes are parallel to each other; and a prism arranged further distally than the first and second axis-shifted lenses, the prism being configured to change a viewing direction of each of the first and second axis-shifted lenses; wherein at least a portion of each of the truncated portions of the first and second axis-shifted lenses is arranged further outward in the radial direction than the prism.

The adapter can further comprise: a holder having a portion configured to attach to and detach from a distal end of the endoscope, the holder including a housing hole in which the first and second axis-shifted lenses are disposed, wherein the housing hole includes first and second cut-out receiving surfaces configured to abut the truncated portion of each of the first and second axis-shifted lenses, respectively, and at least a portion of each of the cut-out receiving surfaces of the holder is arranged further outward in the radial direction than the prism.

The adapter can further comprise: a holder having a portion configured to attach to and detach from a distal end of the endoscope, the holder including a housing hole in which the first and second axis-shifted lenses are disposed, wherein the housing hole includes first and second cut-out receiving surfaces configured to abut the truncated portion of each of the first and second axis-shifted lenses, respectively, the holder further includes one or more prism positioning surfaces having at least a portion that is further outward in a radial direction than the first and second truncated receiving surfaces, the prism abutting on the one or more prism positioning surfaces to position the prism in the holder, the one or more prism positioning surfaces each including a side surface, and at least a portion of each of the cut-out receiving surfaces of the holder is arranged further outward in the radial direction than a respective one the side surfaces.

DETAILED DESCRIPTION

Figure 1:
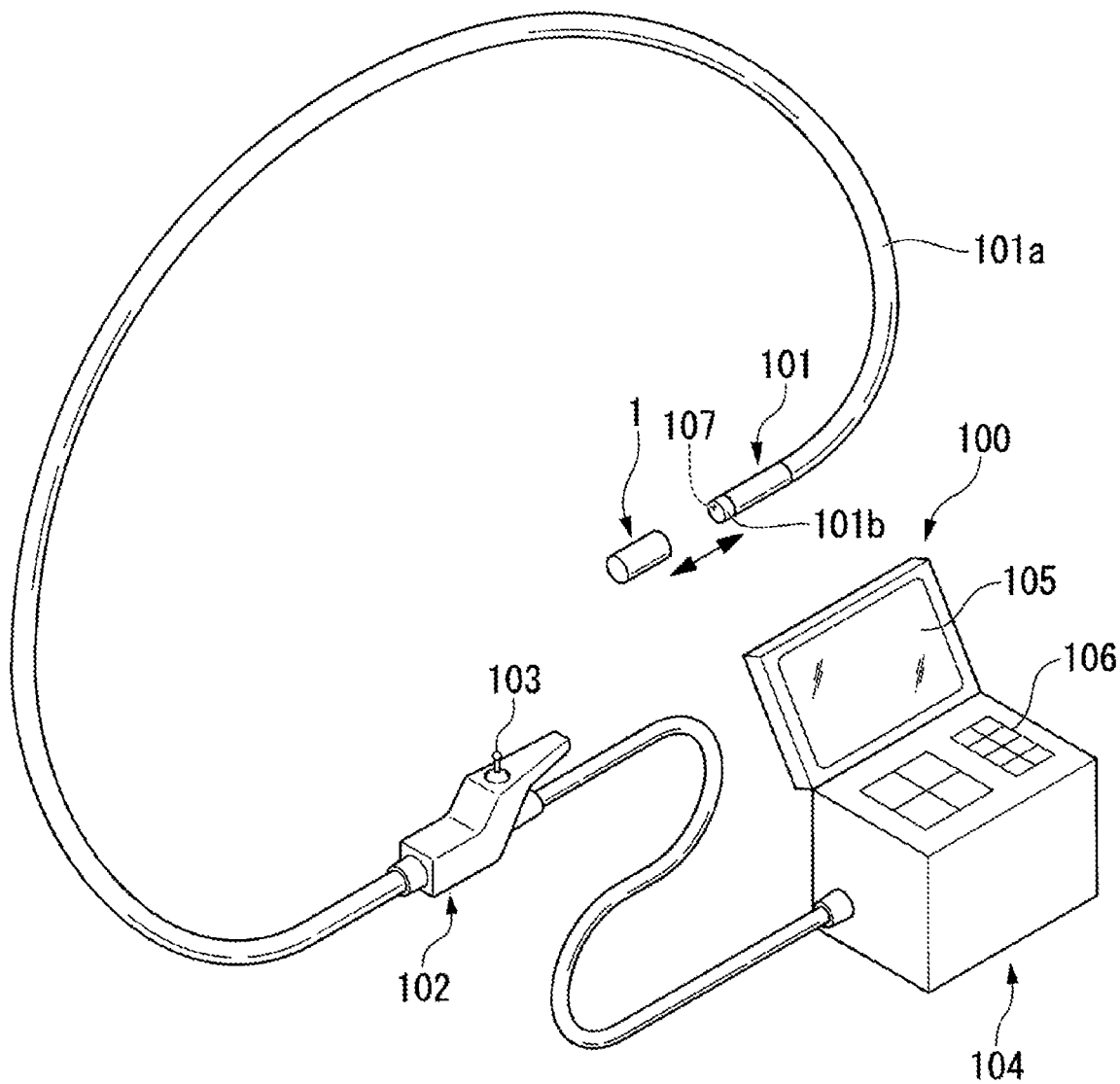
FIG. 1 illustrates a side-viewing optical adapter according to an embodiment and an endoscope to which the side-viewing optical adapter is attached.

A side-viewing optical adapter according to an embodiment will be described. FIG. 1 illustrates a side-viewing optical adapter (hereinbelow referred to as "an adapter") 1 according to the present embodiment and an endoscope 100 to which the adapter 1 is attached.

The endoscope 100 has a known basic configuration and, as illustrated in FIG. 1, includes an elongated endoscope inserting unit 101, an operating unit 102, and an operating unit main body 104. The endoscope inserting unit 101 has an observation optical system 107 at a tip end thereof. The operating unit 102 includes a joystick 103, a display unit 105, an operation panel 106, and the like and is connected to the endoscope inserting unit 101. The joystick 103 is an operating unit configured to allow the endoscope inserting unit 101 to be operated. The display unit 105 displays an image of an inside of an object to be inspected obtained in the endoscope inserting unit 101. The operation panel 106 is provided to allow various operations of the endoscope 100 to be performed. The operating unit main body 104 is connected to not-illustrated battery and AC power supply and is configured to enable electric power to be supplied to a circuit board (not illustrated) provided inside the operating unit main body, the observation optical system 107 provided at the tip end portion of the endoscope inserting unit 101, and the like.

Figure 2:
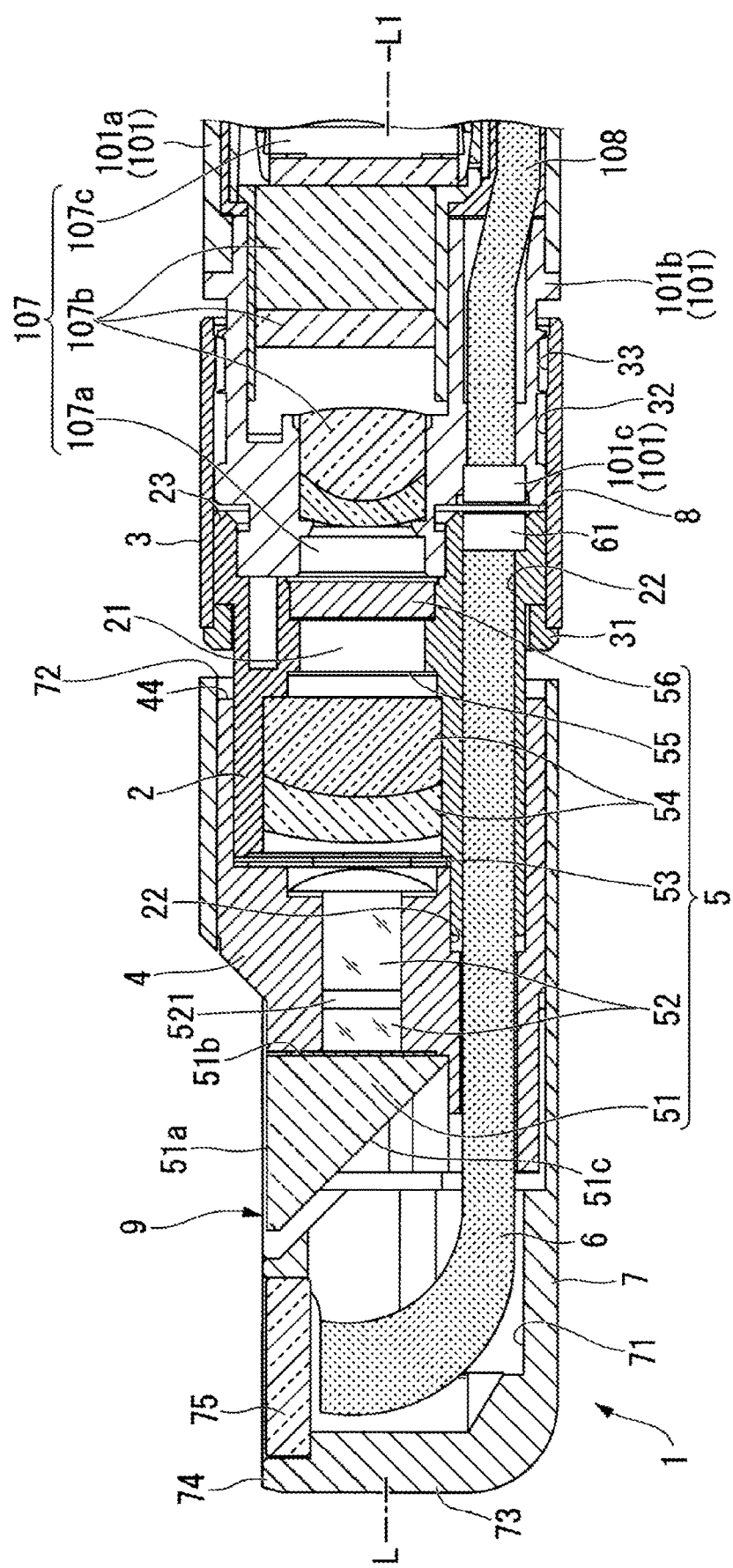
FIG. 2 is a cross-sectional view illustrating a state in which the side-viewing optical adapter according to the embodiment is attached to an endoscope inserting unit.
Figure 3:
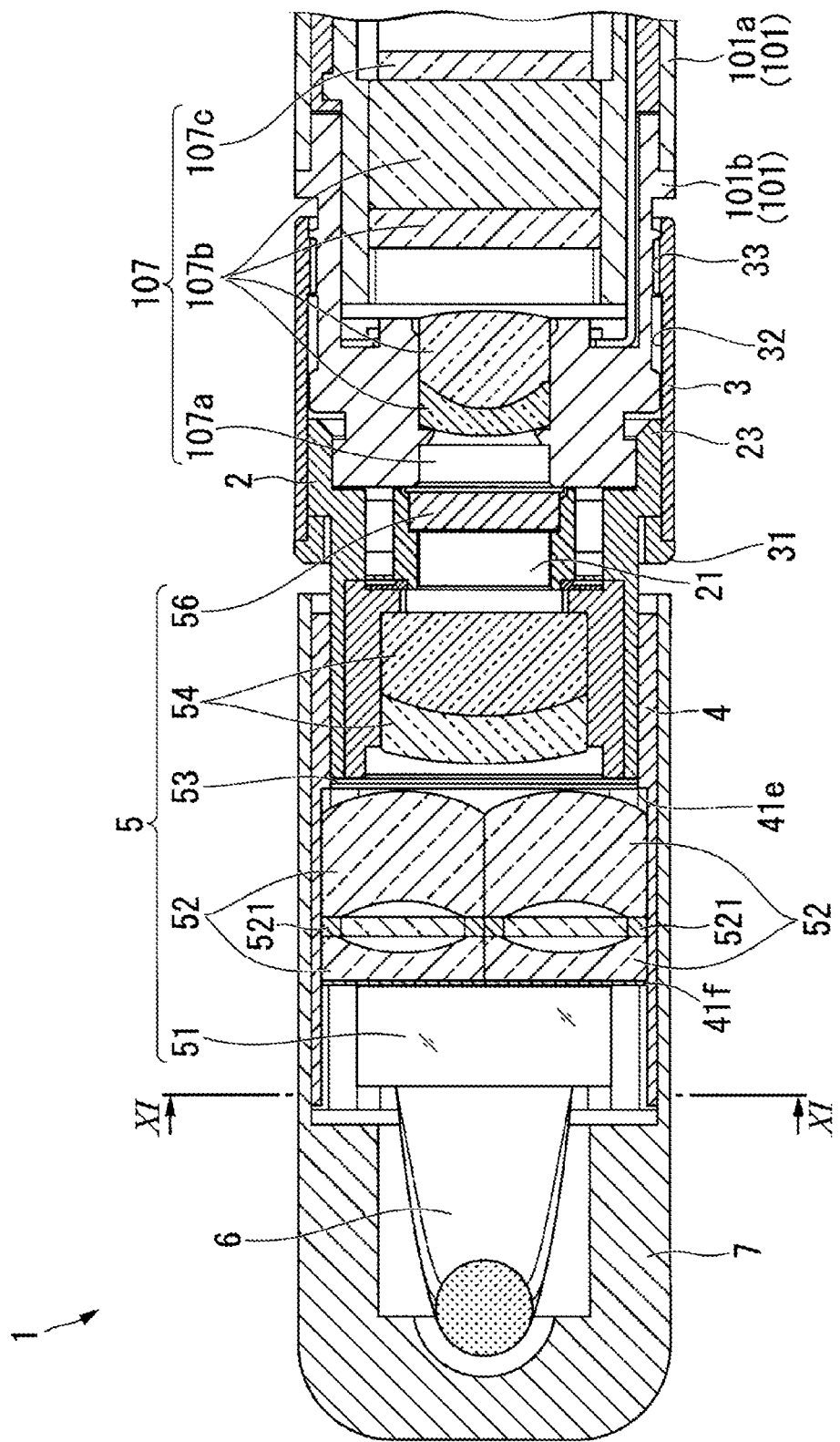
FIG. 3 is a cross-sectional view illustrating a state in which the side-viewing optical adapter according to the embodiment is attached to the endoscope inserting unit.

Each of FIGS. 2 and 3 is a cross-sectional view illustrating a state in which the adapter 1 is attached to the endoscope inserting unit 101 and is a cross-sectional view along a longitudinal axis L1 of the endoscope inserting unit 101. FIG. 3 is a cross-sectional view in a direction perpendicular to the cross-section of FIG. 2. In the following description, in a case in which the adapter 1 is attached to the tip end of the endoscope inserting unit 101, an extension of the longitudinal axis L1 of the endoscope inserting unit 101 will be referred to as a longitudinal axis L of the adapter 1. In the endoscope inserting unit 101, a portion from a base end connected to the operating unit 102 to the tip end portion is a soft tube 101a. The tip end portion of the soft tube 101a is connected to a hard tube 101b.

As illustrated in FIGS. 2 and 3, the observation optical system 107 of the endoscope inserting unit 101 is held inside the hard tube 101b. The observation optical system 107 includes an observation window 107a, an inserting unit tip end lens group 107b, a solid-state image pickup device 107c, a control board (not illustrated), and a signal line (not illustrated) in this order from the tip end of the hard tube 101b. The observation window 107a is a glass cover arranged on the tip end surface of the endoscope inserting unit 101. The inserting unit tip end lens group 107b is provided further on the base end side than the observation window 107a, and a plurality of lenses are arrayed and fixed along the axis of the endoscope inserting unit 101 with optical axes thereof aligned.

The solid-state image pickup device 107c is an image sensor represented by a CCD and a CMOS. The signal line is connected to the solid-state image pickup device 107c, passes through the hard tube 101b and the soft tube 101a, and is connected to a signal processing circuit (not illustrated) in the operating unit main body 104 (refer to FIG. 1). The signal line transmits a control driving signal of the solid-state image pickup device 107c transmitted via the control board and an image signal of an inspected part generated in the solid-state image pickup device 107c.

On the lateral side of the observation optical system 107 inside the hard tube 101b, an inserting unit light guide 108 is provided along the direction of the longitudinal axis L1 of the hard tube 101b. The tip end of the inserting unit light guide 108 is connected to a connecting unit 101c fixed to the tip end of the hard tube 101b, and the base end thereof passes through the passage of the hard tube 101b and the soft tube 101a and is connected to the operating unit main body 104 (refer to FIG. 1).

As illustrated in FIG. 2, the adapter 1 includes a main body (main body unit) 2, a hood 3, a lens holding member (holding member) 4, an adapter optical system 5, a light guide 6, and a cover 7. The adapter 1 is a side-viewing stereo optical adapter. The adapter 1 has an observation surface 9 in a direction perpendicular to the longitudinal axis L of the adapter 1. In the following description, a side provided with the observation surface 9 of the adapter 1 will be referred to as an upper side (upper side in FIG. 2), an opposite side of the observation surface with the center axis interposed therebetween will be referred to as a lower side, and a direction at 90 degrees to the observation surface as seen along the center axis will be referred to as a width direction.

The adapter optical system 5 includes a prism 51, a pair of axis-shifted lenses 52, a focus adjusting unit 53, a backside lens 54, a brightness diaphragm 55, and an observation window 56 in this order from the tip end. As the focus adjusting unit 53, the backside lens 54, and the brightness diaphragm 55, known ones can be used. The backside lens 54, the brightness diaphragm 55, and the observation window 56 are held in the main body 2. The backside lens 54 and the brightness diaphragm 55 are arranged with optical axes thereof aligned. The prism 51, the pair of axis-shifted lenses 52, and the focus adjusting unit 53 are held in the lens holding member 4.

Figure 8:
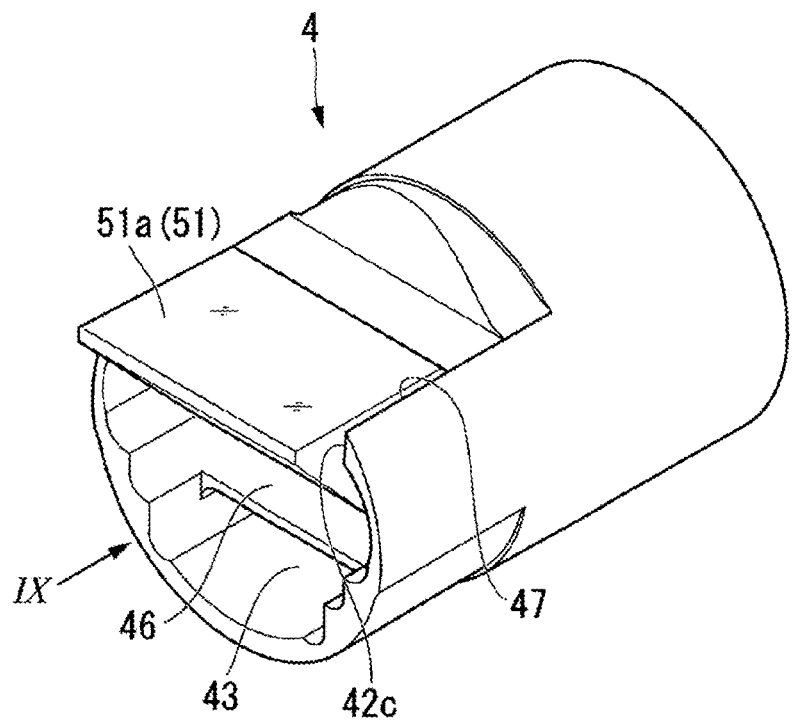
FIG. 8 is a perspective view illustrating a state in which the axis-shifted lenses and a prism are arranged in the holding member according to the embodiment.

As illustrated in FIGS. 2 and 8, the prism 51 is formed approximately in a triangular prismatic shape. The prism 51 is arranged further on the tip end side than the pair of axis-shifted lenses 52. The prism 51 includes a first surface 51a provided to be parallel to the observation surface 9, a second surface 51b perpendicular to the first surface 51a and opposed to the axis-shifted lenses 52, an inclined surface 51c, and a side surface 51d. The inclined surface 51c is provided with a reflection surface. The prism 51 is configured to change a traveling direction of light taken from the observation surface 9 provided on the upper side of the adapter 1 into a base end direction along the direction of the longitudinal axis L of the adapter 1 by means of the reflection surface.

Figure 4:
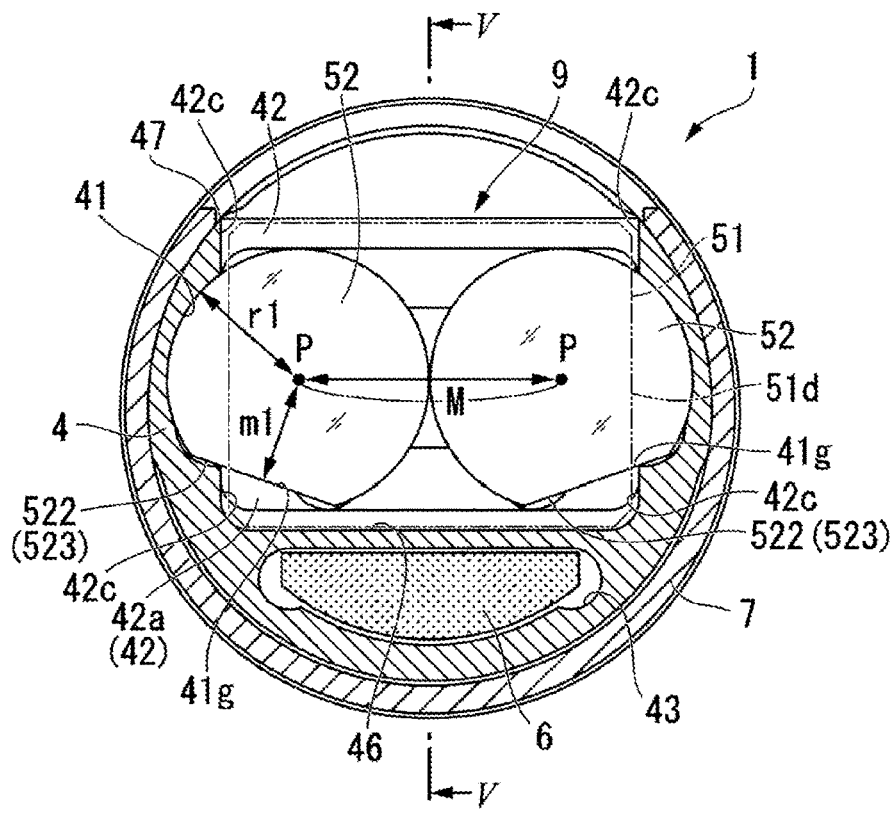
FIG. 4 is a cross-sectional view of the side-viewing optical adapter along the line XI-XI illustrated in FIG. 3 as seen from a tip end side.
Figure 7:
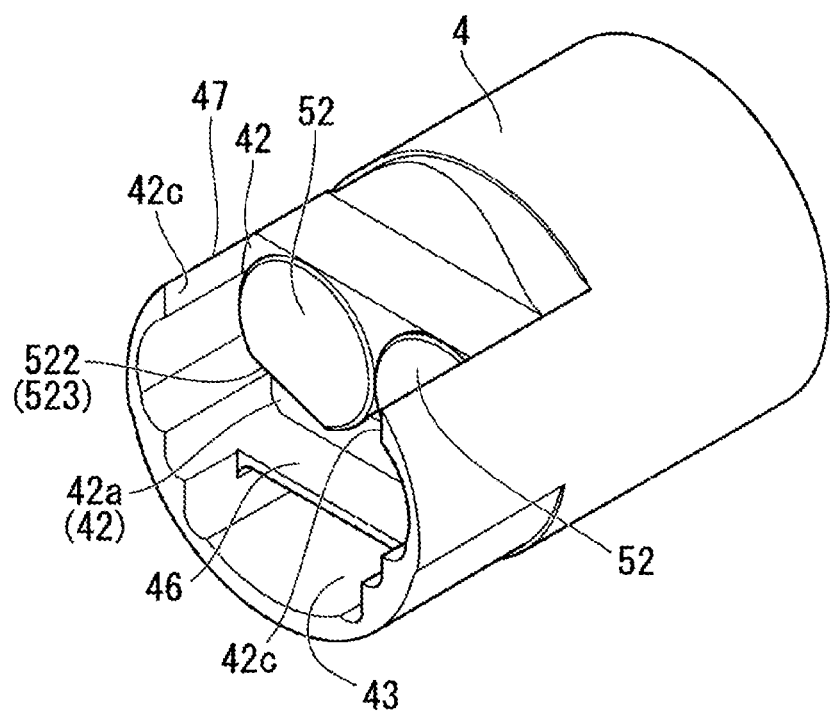
FIG. 7 is a perspective view illustrating axis-shifted lenses and the holding member according to the embodiment.

As illustrated in FIG. 3, the axis-shifted lenses 52 as a pair are arranged side by side so that the respective optical axes may be parallel. Specifically, the respective optical axes of the axis-shifted lenses 52 as a pair are arranged side by side in the width direction of the adapter 1. As illustrated in FIGS. 2 and 3, the two axis-shifted lenses 52 are arranged side by side with a spacer ring 521 interposed in each of the two axis-shifted lenses 52 in the direction of the longitudinal axis L. As illustrated in FIGS. 4 and 7, each of the axis-shifted lenses 52 has a truncated portion 522 obtained by a portion of a circular cross section of the axis-shifted lens being removed. The truncated portion 522 includes a cut-out surface 523 extending in parallel with the optical axes of the axis-shifted lenses 52.

The main body 2 is a tubular member located at the base end portion of the adapter 1. As illustrated in FIG. 2, in the main body 2, two lumens (a first lumen 21 and a second lumen 22) passing through the main body 2 in the direction of the longitudinal axis L are formed. In the first lumen 21, the backside lens 54, the brightness diaphragm 55, and the observation window 56 are arranged and fixed in this order from the tip end side. In the second lumen 22 provided to be parallel to the first lumen 21, the light guide 6 passes.

The hood 3 is formed approximately in a cylindrical shape and is connected to the base end portion of the main body 2 via a ring 31. The hood 3 is arranged coaxially with the main body 2 and is connected to the main body 2 to be rotatable around the center axis of the main body 2. An inner circumferential surface 32 of the hood 3 on the base end side is provided with a retaining portion 33 to be engaged with the hard tube 101b.

Figure 5:
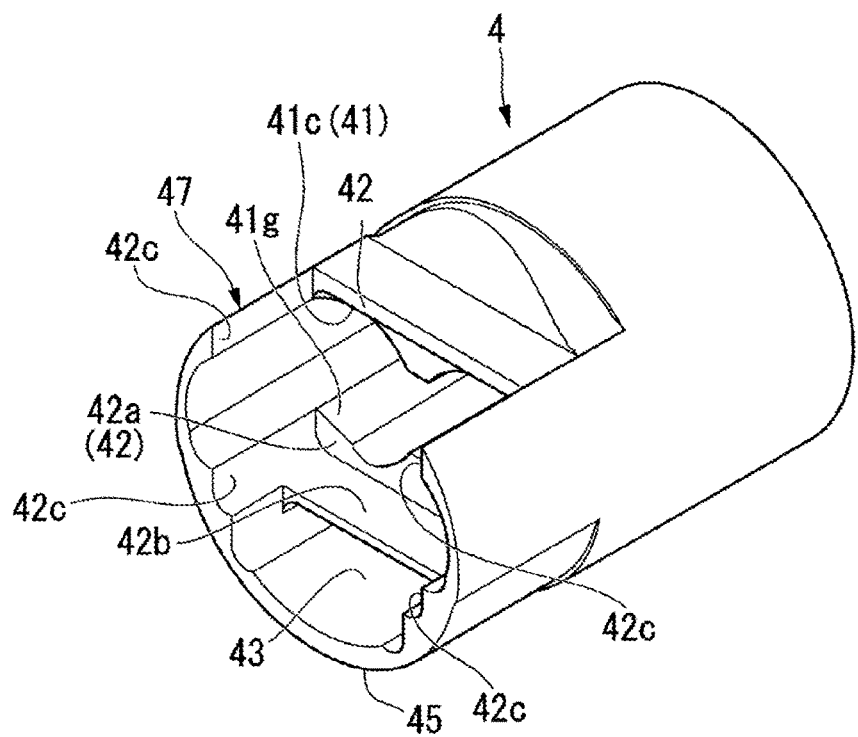
FIG. 5 is a perspective view illustrating a holding member according to the embodiment.
Figure 6:
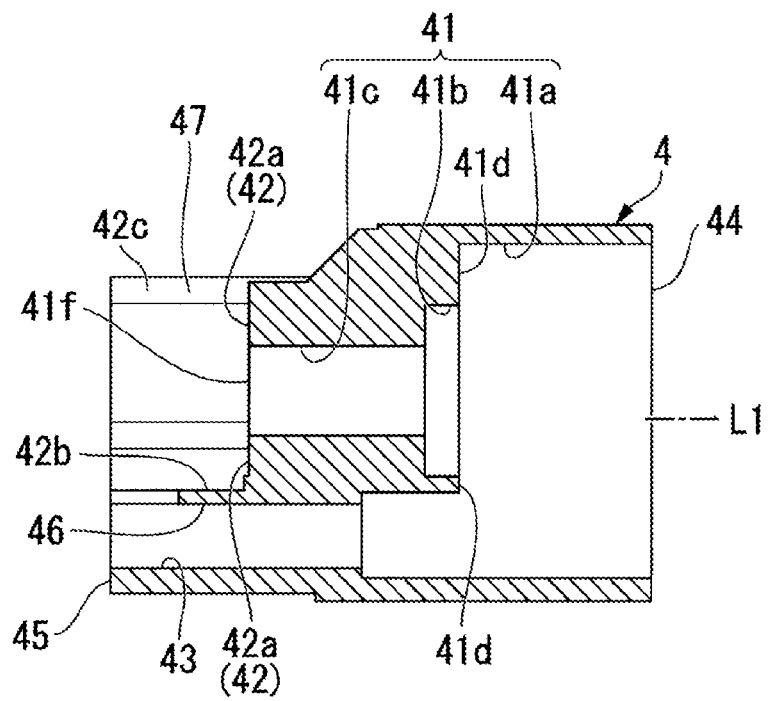
FIG. 6 is a cross-sectional view illustrating the holding member according to the embodiment.

FIG. 5 is a perspective view illustrating the lens holding member 4. FIG. 6 is a cross-sectional view of the lens holding member 4 in an up-down direction along the direction of the longitudinal axis L of the lens holding member 4 (a cross-sectional view based on the line V-V illustrated in FIG. 4). As illustrated in FIGS. 2 to 6, the lens holding member 4 includes a lens housing hole (housing hole) 41, a prism positioning surface 42, and a light guide housing hole 43. The lens housing hole 41 and the light guide housing hole 43 are formed to extend in parallel from a base end opening portion 44 of the lens holding member 4 along the direction of the longitudinal axis L of the lens holding member 4. The light guide housing hole 43 extends to a tip end 45 of the lens holding member 4 and is opened. On the tip end side of the lens housing hole 41, the prism positioning surface 42 is formed. In the lens housing hole 41, the lens group of the adapter optical system 5 including the pair of axis-shifted lenses 52 is inserted and fixed at a predetermined position.

As illustrated in FIGS. 2, 4, and 5, the inner circumferential surface of the lens housing hole 41 is formed to enable the lens group of the adapter optical system 5 to be held at the predetermined position. The lens housing hole 41 includes a first hole portion 41a, a second hole portion 41b, and a third hole portion 41c in this order from the base end opening portion 44. The first hole portion 41a has a dimension enabling the main body 2 to be inserted therein. As illustrated in FIG. 6, the second hole portion 41b has a shorter opening diameter in the up-down direction than that of the first hole portion 41a, and a step portion 41d is formed between the first hole portion 41a and the second hole portion 41b.

In the third hole portion 41c, the pair of axis-shifted lenses is arranged. Thus, the third hole portion 41c is formed to conform to the pair of axis-shifted lenses in terms of the arranging position and the shape. The third hole portion 41c has a cut-out receiving surface 41g abutting on the truncated portion 522 of each of the axis-shifted lenses 52. As illustrated in FIG. 3, the opening dimension of the third hole portion 41c in the width direction is longer than that of the first hole portion 41a. That is, the base end of the third hole portion 41c is shortened in diameter in the width direction, and as illustrated in FIG. 3, a first wall portion (wall portion) 41e facing the third hole portion 41c is formed between the tip end opening edge of the second hole portion 41b and the base end opening edge of the third hole portion 41c. The third hole portion 41c has an equal cross-sectional shape from a tip end opening portion 41f to the first wall portion 41e.

The light guide housing hole 43 is formed further on the tip end side than the step portion 41d and on the lower side of the second hole portion 41b and the first hole portion 41a. That is, the tip end of the first hole portion 41a communicates into the second hole portion 41b and the light guide housing hole 43.

As illustrated in FIG. 6, the tip end of the lens housing hole 41 is located further on the base end side than the tip end 45 of the lens holding member 4. The lens holding member 4 includes around the tip end of the lens housing hole 41 an upper side opening 47 produced by cutting out the upper portion of the lens holding member 4. The lens holding member 4 includes a second wall portion 46 formed on the upper side of the light guide housing hole 43 and further on the tip end side than the lens housing hole 41.

The prism positioning surface 42 includes a base end surface 42a located on the base end side, a lower surface 42b, and a side surface 42c. The base end surface 42a is a surface perpendicular to the longitudinal axis L. The lower surface 42b is a part of the upper surface of the second wall portion 46. The side surface 42c is formed to extend between the tip end of the lens housing hole 41 and the upper side opening 47 of the lens holding member 4 in the up-down direction. The side surface 42c is formed to extend at the edge portion of the upper side opening 47 of the lens holding member 4 in the direction of the longitudinal axis L. The position of the second surface 51b of the prism 51 in the direction of the optical axis is determined at the base end surface 42a. The position of the prism 51 in the up-down direction is determined at the lower surface 42b. The position and the angle of the prism 51 in the width direction are determined at the side surface 42c.

As illustrated in FIG. 2, the cover 7 is located at the tip end portion of the adapter 1 and includes a lumen 71. The lumen 71 extends along the longitudinal axis L from a base end 72 to a tip end surface 73 and is opened to an upper surface 74 on the tip end side. The lumen 71 houses therein the lens holding member 4, the prism 51, and the light guide 6.

Figure 9:
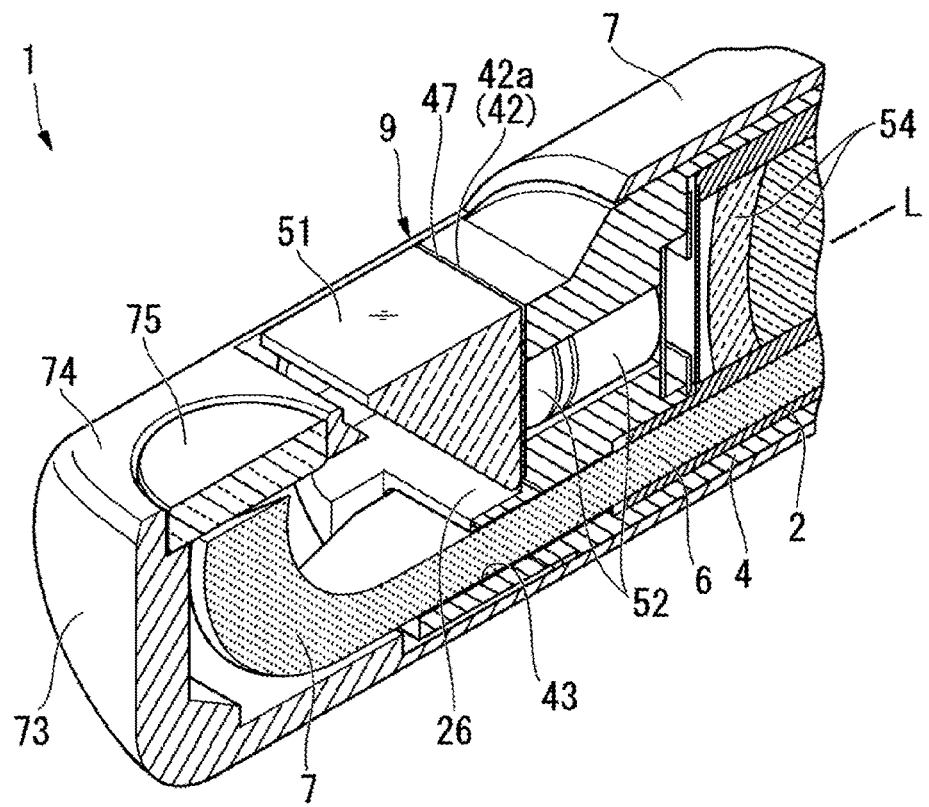
FIG. 9 is a partially exploded perspective view of a tip end portion of the side-viewing optical adapter according to the embodiment.
Figure 10:
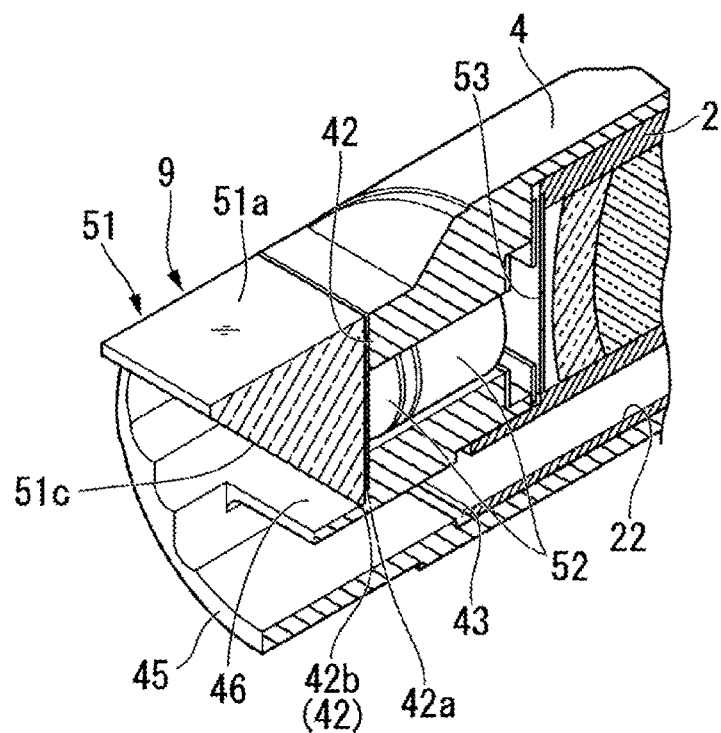
FIG. 10 illustrates a part of the side-viewing optical adapter according to the embodiment and is a partially exploded perspective view.
Figure 11:
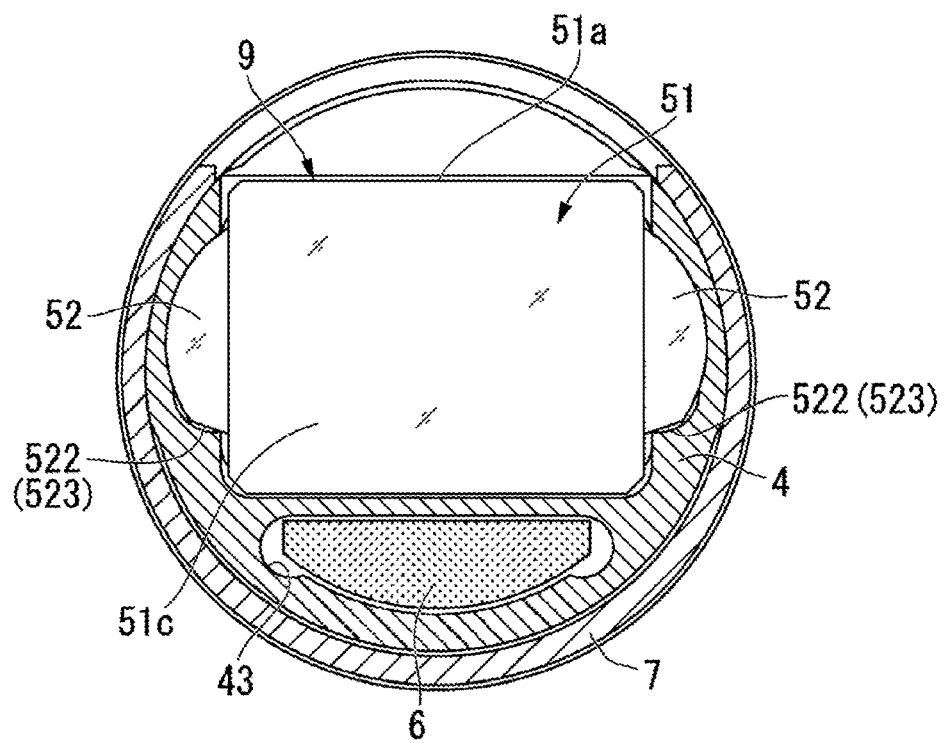
FIG. 11 is a cross-sectional view of the side-viewing optical adapter according to the embodiment in a circumferential direction along the line XI-XI illustrated in FIG. 3.

Next, arrangement of the adapter optical system 5 in the lens holding member 4 will be described. FIG. 7 is a perspective view illustrating the lens holding member 4 in which the pair of axis-shifted lenses 52 is arranged. FIG. 8 is a perspective view illustrating the lens holding member 4 in which the pair of axis-shifted lenses 52 and the prism 51 are arranged. FIG. 9 is a cross-sectional view of the tip end portion of the adapter 1 in the up-down direction along the longitudinal axis L. FIG. 10 is a cross-sectional view illustrating the lens holding member 4 and the adapter optical system 5 out of FIG. 9. FIG. 11 is a cross-sectional view of the adapter 1 along the line XI-XI illustrated in FIG. 3.

The pair of axis-shifted lenses 52 is inserted from the tip end side and is fixed in the third hole portion 41c of the lens housing hole 41. Each of the axis-shifted lenses 52 as a pair is arranged so that the truncated portion 522 may abut on the cut-out receiving surface 41g as illustrated in FIGS. 4 and 7. Since the axis-shifted lenses 52 as a pair are arranged at positions at which the respective arc portions may contact each other, a base-line length M is approximately twice as long as the radius of each axis-shifted lens 52. The two cut-out receiving surfaces 41g are provided to be inclined to the horizontal direction (width direction) further on the lower side than the center of the third hole portion 41c in the up-down direction and on the outer side in the width direction. The two cut-out receiving surfaces 41g are formed to be symmetric across the center of the third hole portion 41c in the width direction.

As illustrated in FIGS. 2 and 8 to 10, the prism 51 is arranged on the tip end side of the axis-shifted lenses 52 to be opposed to the tip end surfaces of the axis-shifted lenses 52. The prism 51 abuts on and is positioned to the prism positioning surface 42 around the tip end opening portion 41f of the lens housing hole 41 and is fixed by means of adhesive or the like. The second surface 51b of the prism 51 abuts on the base end surface 42a of the prism positioning surface 42 to cause the position of the prism 51 in the direction of the optical axis to be defined. The lower end of the prism 51 abuts on and is supported by the lower surface 42b of the prism positioning surface 42. The side surface 51d of the prism 51 in the width direction abuts on the side surface 42c of the prism positioning surface 42 to cause the position and the angle of the prism 51 in the width direction to be defined. The dimension of the prism 51 in the width direction is shorter than the length between the end portions of the paired axis-shifted lenses 52 in the width direction arranged in the third hole portion 41c (the length approximately twice as long as the diameter of each of the axis-shifted lenses 52). As illustrated in FIGS. 4 and 11, at least a part of each truncated portion 522 of each of the axis-shifted lenses 52 as a pair is arranged further on the outer side in the width direction than the prism 51.

As described above, in the conventional configuration, in a case in which the base-line length (refer to FIG. 4) of the pair of axis-shifted lenses is extended further, the abutting area between the circumference of the tip end opening portion of the lens housing hole and the second surface of the prism, and the abutting area between the side surface (lower side) of the prism positioning surface and the side surface of the prism, are smaller, which makes it difficult to hold the prism in a stable manner by means of the lens holding member. Another way that can be conceived of is to further enlarge the abutting area between the circumference of the tip end opening portion of the lens housing hole and the second surface of the prism. However, to secure a sufficient amount of light by means of the light guide, the area of the light guide housing hole cannot be reduced to a predetermined amount or less. Also, in a case in which, to enlarge the prism without changing the dimension of the outside diameter of the adapter, the thicknesses of the cover of the adapter and the lens holding member are thinned, the rigidity will be lowered, which is not favorable. Further, when the prism is enlarged, the entire length of the adapter is extended, and the length of the hard portion of the endoscope inserting unit provided further on the tip end side than the soft tube of the endoscope inserting unit is extended. In a case in which the hard portion at the tip end region of the endoscope inserting unit is long, operability of the endoscope is lowered.

Conversely, in the adapter 1 according to the present embodiment, the positions of the axis-shifted lenses 52 as a pair in the width direction are arranged further on the outer side, and the longer base-line length M is secured. Also, as illustrated in FIG. 4, a distance m1 between the truncated portion 522 and an optical axis P is shorter than a radius r1 of the axis-shifted lens 52. Thus, the prism positioning surface 42 secures a large area of a portion formed in a position closer to the edge portion of the lens holding member 4 than the cut-out receiving surface 41g. Since the adapter 1 according to the present embodiment includes the cut-out receiving surface 41g, the areas of the base end surface 42a and the side surface 42c of the prism positioning surface 42, to be positioned to the prism 51, in the lens holding member 4 around the tip end of the axis-shifted lenses 52 are enlarged. The area of the side surface 42c on the lower side of the prism positioning surface 42 illustrated in FIG. 4 can be set to be larger, and the abutting area between the prism 51 and the lens holding member 4 can be set to be large. As a result, while the long base-line length M is secured, the prism 51 can be held in a stable manner.

The main body 2 is inserted from the side of the base end opening portion 44 of the lens housing hole 41 so as to abut on the focus adjusting unit 53 provided at the step portion 41d. This configuration causes the backside lens 54 to be positioned. As for the lens housing hole 41, further on the tip end side in the direction of the longitudinal axis L than the middle region, the opening dimension in the up-down direction decreases, and the opening dimension in the width direction is adapted to enable the pair of axis-shifted lenses 52 to be arranged side by side in the width direction.

The main body 2 is inserted from the base end opening portion 44 of the lens housing hole 41, and the main body 2 and the lens holding member 4 are engaged. To secure the longer base-line length M of the pair of axis-shifted lenses 52, the outside diameter of the lens holding member 4 is set to be large, and the lens holding member 4 is thus fitted onto the main body 2. Since the external portion of the main body 2 and the lens housing hole 41 of the lens holding member 4 are respectively formed in round shapes, displacement in the circumferential direction between the main body 2 and the lens holding member 4 can be prevented, and the adapter optical system 5 can be positioned at a desired position.

As illustrated in FIG. 2, the light guide 6 is inserted in the light guide housing hole 43 and the second lumen 22. An adapter-side connecting unit 61 is provided at the base end of the second lumen 22. The base end of the light guide 6 is connected to the adapter-side connecting unit 61. The tip end of the light guide 6 is arranged to be curved toward the opening on the upper surface 74 of the cover 7 and is connected to an observation window 75 arranged in the opening of the upper surface 74.

Next, an aspect in which the adapter 1 is attached to the tip end of the endoscope inserting unit 101 will be described.

A user inserts the tip end of the endoscope inserting unit 101 from the base end side of the hood 3 and turns the hood 3 while holding the cover 7 to cause the endoscope inserting unit 101 to be inserted into a base end opening 23 of the main body 2 until the observation window 107a of the endoscope inserting unit 101 abuts on the observation window 56 of the adapter optical system 5. As a result of this operation, the retaining portion 33 of the hood 3 and the hard tube 101b of the endoscope inserting unit 101 are engaged. When the retaining portion 33 of the hood 3 and the hard tube 101b of the endoscope inserting unit 101 are engaged, the optical axis of the observation optical system 107 and the optical axes of the brightness diaphragm, the backside lens, and the focus adjusting unit of the adapter optical system 5 correspond. In this state, the position of the adapter 1 in the direction of the longitudinal axis L1 in relation to the endoscope inserting unit 101 is fixed at a predetermined position.

When the user turns on the illumination in the operating unit main body 104, light transmits to the inserting unit light guide 108, the connecting unit 101c, the adapter-side connecting unit 61, and the light guide 6 in this order, and light is emitted from the observation window 75.

In a case in which observation of the object to be inspected is finished, or in a case in which the adapter type is changed to one required for observation of the object to be inspected, the user turns the hood 3 in a reverse direction of the direction at the time of attaching the adapter 1 while holding the cover 7 to detach the adapter 1 from the tip end of the endoscope inserting unit 101. In this manner, the adapter 1 is configured to be attachable and detachable to and from the tip end of the endoscope inserting unit 101.

The adapter 1 according to the present embodiment has a configuration in which the axis-shifted lenses 52 are provided with the truncated portions 522 to secure the prism positioning surface 42. Accordingly, the base-line length M of the pair of right and left axis-shifted lenses 52 can be extended without degrading holding performance of the prism, and measurement accuracy of the endoscope 100 can be improved. Also, since the prism positioning surface 42 is secured while the base-line length M of the pair of axis-shifted lenses 52 is extended, the prism 51 can be held at an appropriate position. Consequently, the adapter 1 can prevent angular deflection caused by displacement of the prism 51 and degradation of measurement accuracy.

In the adapter 1 according to the present embodiment, the base-line length M of the axis-shifted lenses 52 can be extended without extending the dimension of the outside diameter of the adapter 1. Accordingly, a small-sized stereo optical adapter excellent in measurement accuracy can be provided.

In the present embodiment, an example of providing the cut-out receiving surface 41g at the lower portion of the lens housing hole 41 has been illustrated. However, the cut-out receiving surface has only to be provided so that at least a part of the truncated portion 522 of each of the axis-shifted lenses 52 as a pair may be arranged further on the outer side in the width direction than the prism 51. For example, the cut-out receiving surface may be provided close to the outer end portion in the width direction of the upper portion of the lens housing hole 41.

In the present embodiment, an example in which the base-line length M of the pair of axis-shifted lenses 52 is approximately equal to the diameter of the axis-shifted lens 52 has been illustrated. However, the base-line length M of the pair of axis-shifted lenses 52 (distance between center axes of the axis-shifted lenses) may be equal to or longer than the diameter of the axis-shifted lens 52. As described above, the base-line length is favorably longer to improve measurement performance. Thus, the axis-shifted lenses may be arranged so that as a long base-line length as possible can be obtained within the range of the dimension of the outside diameter of the adapter 1.

In the present embodiment, an example in which the prism positioning surface 42 includes the lower surface 42b and the side surface 43c as well as the base end surface 42a has been illustrated. However, the present embodiment is not limited to this. For example, a configuration in which the prism 51 is positioned only by the base end surface that positions the prism 51 in the direction of the optical axis, a configuration in which the prism 51 is positioned by the base end surface and the lower surface, or a configuration in which the prism 51 is positioned by the base end surface and the side surface may be available.

In the present embodiment, although the single-reflection right angle prism formed approximately in a triangular prismatic shape is used, a plural-reflection prism or a prism reflecting light in an oblique direction may be used.

First Modification Example

Figure 12:
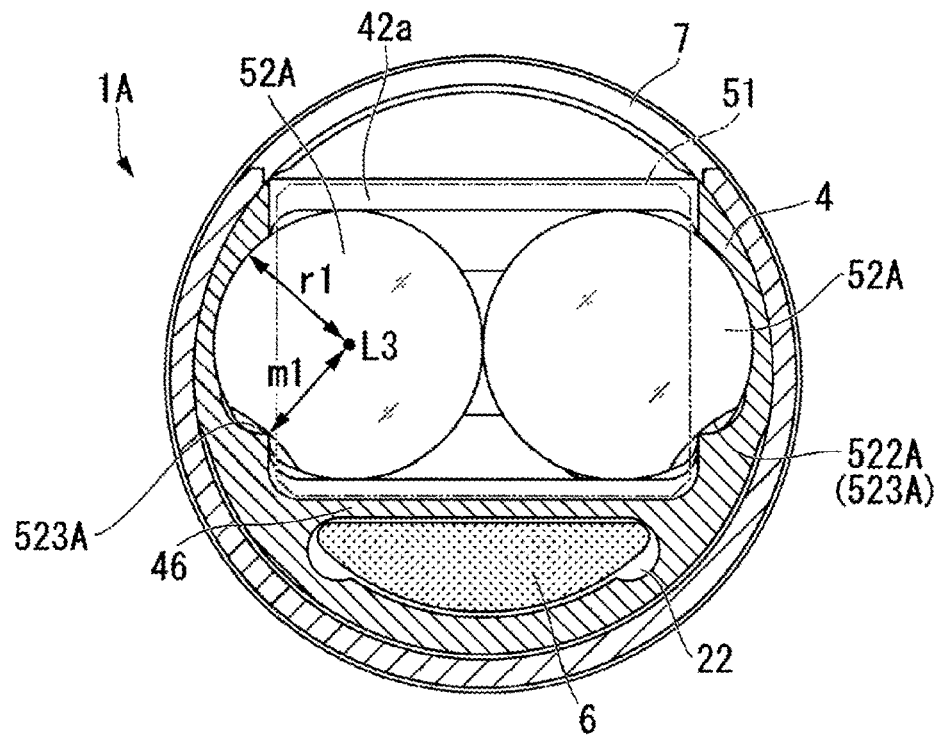
FIG. 12 illustrates a first modification example of the embodiment and is a cross-sectional view in the circumferential direction along the same position as that of the line XI-XI in FIG. 3.

Next, a first modification example of the adapter 1 according to the present embodiment will be described. FIG. 12 illustrates an adapter 1A according to the first modification example of the present embodiment and is a cross-sectional view along the same position as that of the line XI-XI in FIG. 3.

As illustrated in FIG. 12, the shape of a cut-out surface 523A of a truncated portion 522A of each of the axis-shifted lenses 52 as a pair differs from that in the above embodiment. In the present modification example, the cut-out surface 523A projects toward the optical axis of the axis-shifted lens 52 and is a curved surface extending in parallel with the optical axis.

In this manner, the shape of the cut-out surface is not limited to the example illustrated in the above embodiment as long as a part of the outer circumference of each of the axis-shifted lenses 52 is cut out to secure the prism receiving surface. The present modification example has an approximately similar effect to that of the above embodiment in that the prism receiving surface is secured in the lens holding member 4.

Second Modification Example

Next, a second modification example of the adapter 1 according to the present embodiment will be described. Each of FIGS. 13 and 14 illustrates an adapter 1B according to the second modification example of the present embodiment and is a cross-sectional view in the circumferential direction along the same position as that of the line XI-XI in FIG. 3.

Figure 13:
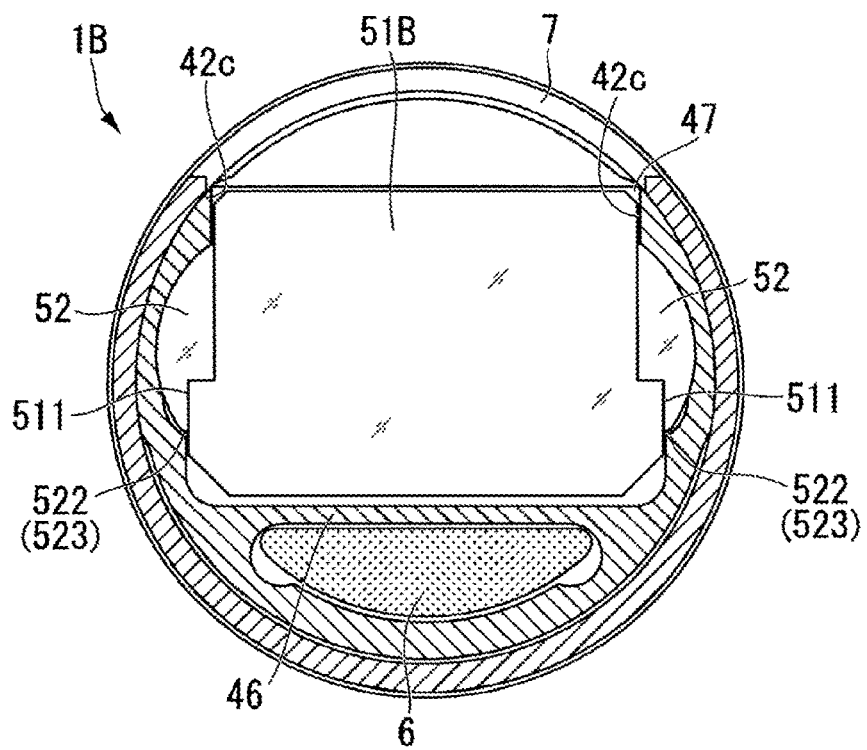
FIG. 13 illustrates a second modification example of the embodiment and is a cross-sectional view in the circumferential direction along the same position as that of the line XI-XI in FIG. 3.
Figure 14:
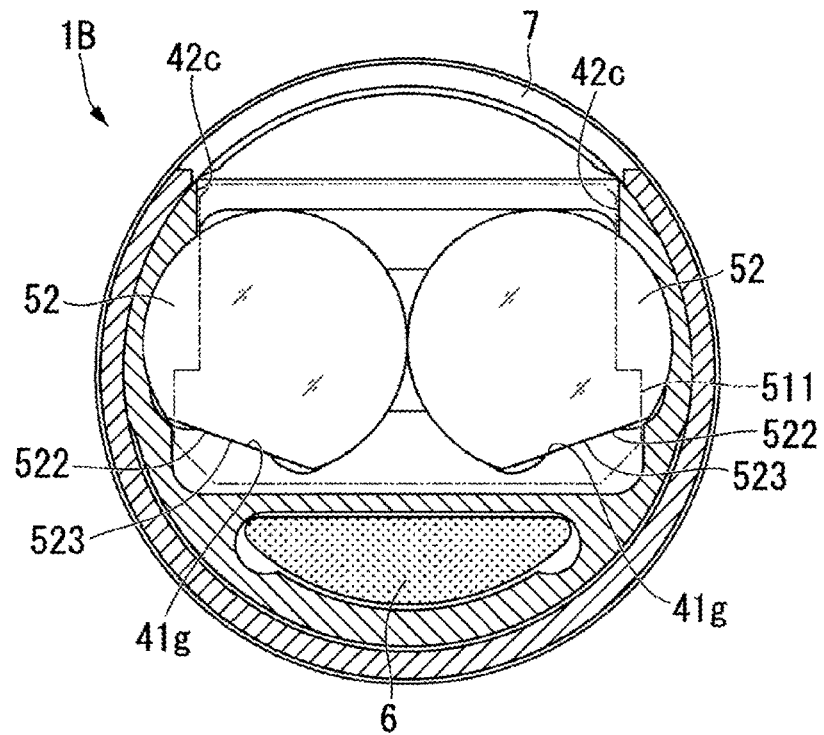
FIG. 14 illustrates the second modification example of the embodiment and is a cross-sectional view in the circumferential direction along the same position as that of the line XI-XI in FIG. 3.

As illustrated in FIG. 13, in the present modification example, a prism 51B differs from that in the above embodiment. In the prism 51B according to the present modification example, the dimension of a lower portion 511 in the width direction is longer than that of the upper portion.

As described above, the adapter 1 is provided at the lower portion 511 with the light guide 6. Thus, the adapter optical system 5 is arranged at the upper portion of the adapter 1. For this reason, as illustrated in FIGS. 13 and 14, since the upper end part of the prism 51B is located close to the inner circumferential surface of the cover 7, the dimension of the prism 51B has restriction. On the other hand, at the lower portion 511 of the prism 51B, the thicknesses of the lens holding member 4 ranging from the side surface 42c of the prism positioning surface 42 to the outside of the adapter 1 and the cover 7 are large. Thus, the dimension of the lower portion 511 of the prism 51B in the width direction can be extended. As a result, at the lower end portion of the prism 51B, the abutting area between the prism positioning surface 42 and the lower portion 511 of the prism 51B can be set to be large. Accordingly, the present modification example has a similar effect to that of the above embodiment, and the prism 51B can be held in a more stable manner.

Third Modification Example

Figure 15:
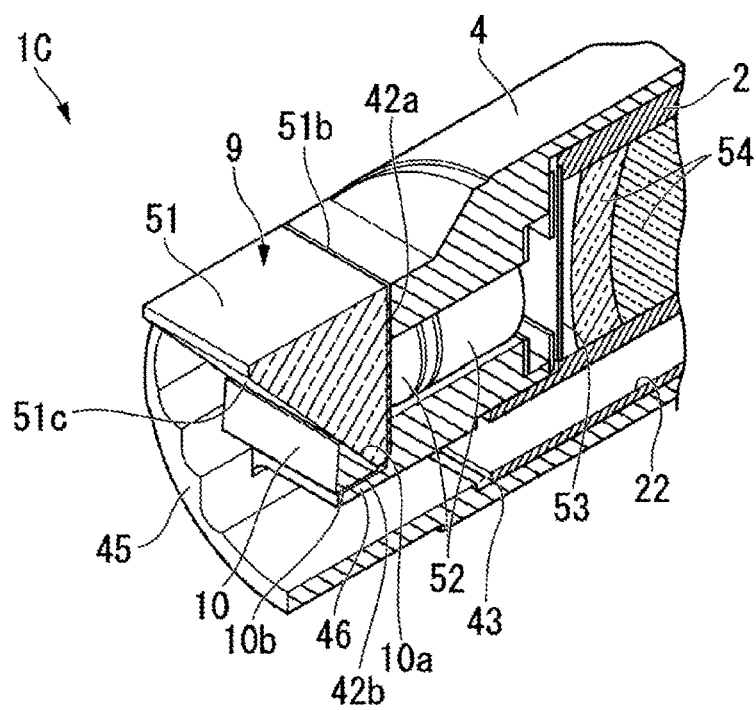
FIG. 15 illustrates a part of a side-viewing optical adapter according to a third modification example of the embodiment and is a partially exploded perspective view.

Next, a third modification example of the adapter 1 according to the present embodiment will be described. FIG. 15 is a cross-sectional view in the up-down direction illustrating an adapter 1C according to the third modification example of the present embodiment. As illustrated in FIG. 15, the present modification example is an example provided with a supporting member 10 that supports the prism 51. The supporting member 10 is formed approximately in a triangular prismatic shape, and an inclined surface 10a contacts the inclined surface 51c of the prism 51. At the time of arranging the prism 51, a lower surface 10b of the supporting member 10 is mounted on the lower surface 42b of the prism positioning surface 42, and the second surface 51b of the prism 51 abuts on the base end surface 42a of the prism positioning surface 42.

The present modification example has a similar effect to those of the above embodiment and the second modification example. In addition, since the material for the supporting member does not need to be glass, the supporting member is produced more easily than the prism 51B according to the second modification example.

Although the embodiment has been described above with reference to the drawings, the specific configuration is not limited to that of the present embodiment, and includes design changes and the like without departing from the scope of the present invention.

Also, the components illustrated in the above embodiment and modification examples can arbitrarily be combined.

INDUSTRIAL APPLICABILITY

It is possible to provide a side-viewing optical adapter enabling a long base-line length of right and left axis-shifted lenses to be secured without degrading holding performance of a prism.

REFERENCE SIGNS LIST

1, 1A, 1B, 1C side-viewing optical adapter
2 main body (main body unit)
4 lens holding member (holding member)
41 housing hole
41e first wall portion (wall portion)
41f tip end opening portion
41g cut-out receiving surface
42 prism positioning surface
51 prism
52 axis-shifted lens
522, 522A truncated portion
54 backside lens
523, 523A cut-out surface

What is claimed is:

1. An adapter for use with an endoscope, the adapter comprising:
   first and second axis-shifted lenses, each of the first and second axis-shifted lenses including a truncated surface formed on an outer cylindrical surface of each of the first and second axis-shifted lenses, the first and second axis-shifted lenses being arranged side by side so that respective first and second optical axes are parallel to each other;
   a prism arranged further distally than the first and second axis-shifted lenses, the prism being configured to change a viewing direction of each of the first and second axis-shifted lenses; and
   a holder having a portion configured to attach to and detach from a distal end of the endoscope, the holder including a housing hole in which the first and second axis-shifted lenses are disposed;
   wherein the housing hole includes first and second cut-out receiving surfaces configured to abut the truncated surface of each of the first and second axis-shifted lenses, respectively;
   the holder further includes one or more prism positioning surfaces having at least a portion that is further outward in a radial direction than the first and second cut-out receiving surfaces, the prism abutting on the one or more prism positioning surfaces to position the prism in the holder;
   at least a portion of each of the truncated surfaces of the first and second axis-shifted lenses is arranged further outward in the radial direction than the prism; and
   the first and second cut-out receiving surfaces are inclined relative to a horizontal plane passing through a center of each of the first and second axis-shifted lenses, the first and second cut-out receiving surfaces being inclined such that an outer portion of the first and second cut-out receiving surfaces is closer to the horizontal plane than an inner portion of the first and second cut-out receiving surfaces.

2. The adapter according to claim 1, further comprising:
   at least one backside lens arranged proximally to the first and second axis-shifted lenses; and a main body configured to hold the at least one backside lens;
wherein the holder having a wall defining the housing hole, the wall having a first portion and a second portion, the second portion being proximal to the first portion;
the first portion having a first thickness in a radial direction that is constant in a longitudinal direction of the holder;
the second portion having a second thickness in the radial direction greater than the first thickness to form a step at a transition between the first portion and the second portion;
the first and second axis-shifted lenses being accommodated in the first portion; and
the main body being accommodated in the second portion.

3. The adapter according to claim 1, wherein the truncated surface of each of the first and second axis-shifted lenses extends parallel with the optical axis.

4. The adapter according to claim 1, wherein the truncated surface of each of the first and second axis-shifted lenses forms a concave surface extending in parallel with the optical axis.

5. The adapter according to claim 4, wherein the concave surface is a curved concave surface.

6. The adapter according to claim 1, wherein the first and second axis-shifted lenses are arranged so that a distance between center axes of the first and second axis-shifted lenses is equal to or longer than a diameter of each of the first and second axis-shifted lenses.

7. The adapter according to claim 1,
wherein the prism positioning surfaces includes a bottom surface, and
the first and second cut-out receiving surfaces are formed on a plane which is offset from a parallel plane and from a vertical plane of the bottom surface.

8. The adapter according to claim 1, wherein the first and second axis-shifted lenses are arranged at positions at which respective outer cylindrical surfaces of the first and second axis-shifted lenses are in contact with each other.

9. The adapter according to claim 1, wherein:
the one or more prism positioning surfaces includes a base end surface perpendicular to a longitudinal axis and configured to determine a position of the prism in a longitudinal axis direction; and
the base end surface and a distal surface of the first and second axis-shifted lenses are arranged to be in parallel to each other.

* * * * *